(12) United States Patent
Dewdney

(10) Patent No.: US 8,135,451 B2
(45) Date of Patent: Mar. 13, 2012

(54) PATIENT SUPPORT TABLE FOR A MAGNETIC RESONANCE SYSTEM HAVING A STRONG MAGNETIC FIELD AND A MAGNETIC RESONANCE SYSTEM INCLUDING SUCH A PATIENT SUPPORT TABLE

(75) Inventor: Andrew Dewdney, Neunkirchen am Brand (DE)

(73) Assignee: Siemens Aktiengesellschaft, Munich (DE)

( * ) Notice: Subject to any disclaimer, the term of this patent is extended or adjusted under 35 U.S.C. 154(b) by 1011 days.

(21) Appl. No.: 11/983,862

(22) Filed: Nov. 13, 2007

(65) Prior Publication Data
US 2008/0132780 A1  Jun. 5, 2008

(30) Foreign Application Priority Data
Nov. 14, 2006  (DE) .................. 10 2006 053 612

(51) Int. Cl.
*A61B 5/05*   (2006.01)

(52) U.S. Cl. ............. 600/410; 600/415; 600/422; 5/601

(58) Field of Classification Search .................. 600/410, 600/415, 422; 5/601
See application file for complete search history.

(56) References Cited

U.S. PATENT DOCUMENTS

| | | | |
|---|---|---|---|
| 4,567,894 A * | 2/1986 | Bergman | 600/415 |
| 2005/0270027 A1 * | 12/2005 | Truong et al. | 324/309 |
| 2006/0042009 A1 | 3/2006 | Somasundaram et al. | |

OTHER PUBLICATIONS

"Modulare pneumatische Linearantriebe"; Origa System Plus; Fa. Hoerbiger-Origa www.hoerbiger.com; März 2006; pp. 1-18.

* cited by examiner

*Primary Examiner* — Long V. Le
*Assistant Examiner* — Joel Lamprecht

(57) ABSTRACT

A patient support table for a magnetic resonance system with a magnetic field generation device creating a magnetic field of 7 T or more, comprising a table plate able to be moved into and out of the patient chamber of the magnetic resonance system by means of a drive device, characterized in that the drive device features a pneumatic cylinder with a piston which is coupled to the table plate, with the pneumatic cylinder featuring two working areas divided via the piston and able to be supplied separately with a working medium.

7 Claims, 2 Drawing Sheets

PATIENT SUPPORT TABLE FOR A MAGNETIC RESONANCE SYSTEM HAVING A STRONG MAGNETIC FIELD AND A MAGNETIC RESONANCE SYSTEM INCLUDING SUCH A PATIENT SUPPORT TABLE

CROSS REFERENCE TO RELATED APPLICATIONS

This application claims priority of German application No. 10 2006 053 612.6 filed Nov. 14, 2006, which is incorporated by reference herein in its entirety.

FIELD OF THE INVENTION

The invention relates to a patient support table for a magnetic resonance system with a magnetic resonance generation device generating a magnetic field of 7 T or more, comprising a movable table plate able to be moved into and out of the patient chamber of the magnetic resonance system by means of a drive device.

BACKGROUND OF THE INVENTION

The magnetic resonance generation devices of modern magnetic resonance systems allow them to create ever more powerful magnetic fields. Systems with a generated field strength of 7 T or more are already known and in use. As the magnetic field strength increases the leakage field extending into the space outside the magnetic resonance system also increases. Neighboring equipment is affected by this leakage field. This strong leakage field is now able to affect the functionality of corresponding components sensitive to said field, meaning that these interactions with the leakage field may result in malfunctions. An example of this would be the electric motor drives of the patient support table which is able to be moved horizontally by means of the electric motor or motors into and out of the patient chamber of the magnetic resonance system. With these types of powerful magnetic resonance systems, as defined above, such electric motors cannot be used for driving the table since their function will be disturbed by the strong leakage field. For this reason the table plate of the patient support table can only be moved manually in powerful magnetic resonance systems of this type, which is tedious for the operators, and the table plate is furthermore not able to be positioned as exactly as would be possible with an automatically driven table.

SUMMARY OF THE INVENTION

The underlying object of the invention is thus to specify a patient support table which makes possible an automatic table plate movement even with the strong leakage fields of the magnetic resonance systems described above.

To resolve this problem the invention makes provision, with a patient support table of the type mentioned at the start, for the drive apparatus to feature a pneumatic cylinder with a piston which is coupled to the table plate, with the pneumatic cylinder featuring working areas divided by the piston and able to be supplied separately with a working medium.

The inventive patient support table basically features a pneumatic table plate drive. This comprises a pneumatic cylinder with a piston which is connected to the table plate. The piston divides the cylinder into two working areas which can each be separately supplied with the working medium, for example simple compressed air. Depending on the working area to which the pressure is now applied, the piston moves in one direction or the other within the pneumatic cylinder. The pneumatic cylinder itself, in view of the considerable length of the magnetic resonance system, of which the magnetic field generation device, because of the strong field to be generated, is much longer than with less powerful systems, must be embodied corresponding long, so that the table plate can be moved fully out of the patient chamber and also driven fully into it. The pneumatic cylinder should preferably essentially be as long as the patient chamber, which, for a 7 T magnetic resonance system, has an axial length of around 6 m, in order to implement a corresponding movement path of the table plate.

Since the table plate movement is controlled pneumatically here, no sensitive electrical or electromechanical components exist in the area of the leakage that could adversely be influenced by the latter. Instead an automatic table plate movement can be implemented using the inventive pneumatic drive device even with extremely powerful magnetic resonance systems. A pneumatic drive is also far safer than a hydraulic drive.

A useful development of the invention makes provision for the pneumatic cylinder to feature a sealing element extending over at least a part of its length which is slit over at least a part of its length and is penetrated by a connecting element connecting the piston to the table plate. This inventive design makes it possible to use a special pneumatic cylinder which can be arranged completely within the patient chamber. Unlike with a normal pneumatic cylinder, in which the connecting rod at one end of the cylinder is able to be moved axially out of the cylinder, with the pneumatic cylinder used in the invention the connecting element passes radially through the cylinder. This requires the cylinder to have an opening running along it through which the connecting element can enter, but with this opening having to be sealed once more above the piston so that the two working areas can be embodied, with a corresponding sealing element being provided which seals off this opening completely. The connecting element penetrates this sealing element, which means that it is embodied so that it opens where the connecting element is but is closed in the remainder of the area. This enables an adequate seal to be achieved in the region of the working areas while at the same time allowing a radial connection to be realized between piston and table plate. This now makes it possible to accommodate the cylinder entirely within the patient chamber and not outside it, as would be the case if a cylinder featuring a normal axial connecting rod were used.

The maximum length of the sealing element is expediently to be dimensioned to the length required for the table plate travel. This can essentially be the entire cylinder length, but can also be less. It is also conceivable to run the sealing element essentially over the entire length of the cylinder but only to embody it with a slit in the area in which the connecting element actually moves.

The sealing element itself is expediently formed from two abutting or overlapping sealing lips. The sealing element or the sealing lips consist of a sufficiently flexible and elastic material which can be moved apart over the connecting element but which at the same time moves back together or overlaps again to form a tight seal once the connection element has passed. The appropriate sufficiently flexible or elastic plastic sealing lips are conceivable which can form a sufficiently tight seal with each other.

The piston itself expediently features two cylinder sections connected via a connecting rod, with the table plate being connected to the connecting rod. The cylinder sections ensure sufficient sealing between the working areas located to the side of them and the area between the cylinder sections, in which the sealing element is penetrated and opened by the connecting element, while the connecting rod simultaneously provides a simple attachment option for the connecting element.

An advantageous development provides for the arrangement of a position detection device for determining the position of the table plate, with the operation of a pump, which is coupled to the working areas via suitable hose connections, able to be controlled as a function of the detection result. A completely automatic and positionally-accurate adjustment mode can be implemented in this way, in accordance with which the exact table plate position can be determined at any point in time via the position detection device and, depending on the detection result, the operation of a pump which, depending on the direction of movement, supplies the one working area with compressed air and sucks air out of the other working area by creating a vacuum, is able to be controlled. Of course a suitable control device is provided via which the operation of the pump can be controlled, with said control device communicating with the position detection device.

The position detection device can preferably be of an optical nature. It includes at least one optical sensor in a fixed position, with corresponding markings in the form of reflectors or such like being provided on the table plate, for example on the underside of the plate. It thus forms a type of light barrier. Since the markings on the table plate are arranged in a predetermined path grid, the actual position of the table plate can be very easily detected in this way and the pump can be controlled on this basis. In addition to an optical position detection or sampling it is of course also conceivable to provide a mechanical position detection for example, by providing suitable mechanical measurement sensors which detect a corresponding mechanical position marking in the form of arresting points or such like on the table plate. This is not a definitive list; any position detection device that allows a sufficiently accurate detection of the actual position of the plate table could be used instead.

The pump itself is connected as described to the working areas via suitable hose connections. This provides the option of arranging the pump itself at any given distance from the magnetic resonance system, and naturally also the assigned control device as well, so that there is no danger of this being able to be in any way adversely affected via the leakage field.

Finally, to enable the table plate to be fixed in a specific position, an arresting device is expediently provided for the table plate, with any type of arresting device being able to be used. This can be arranged for example in the area of a suitable roller or rail guide on which the table plate is supported in the area of the patient cavity or on a frame located outside the patient cavity or can interact with said guide.

Finally the invention further relates to a magnetic resonance system with a magnetic field generation device creating a magnetic field of 7 T or more, including a patient table of the type previously described.

BRIEF DESCRIPTION OF THE DRAWINGS

Further advantages, features and details of the invention emerge from the exemplary embodiment described below and also with reference to the drawings. The figures show.

DETAILED DESCRIPTION OF THE INVENTION

Figure 1:
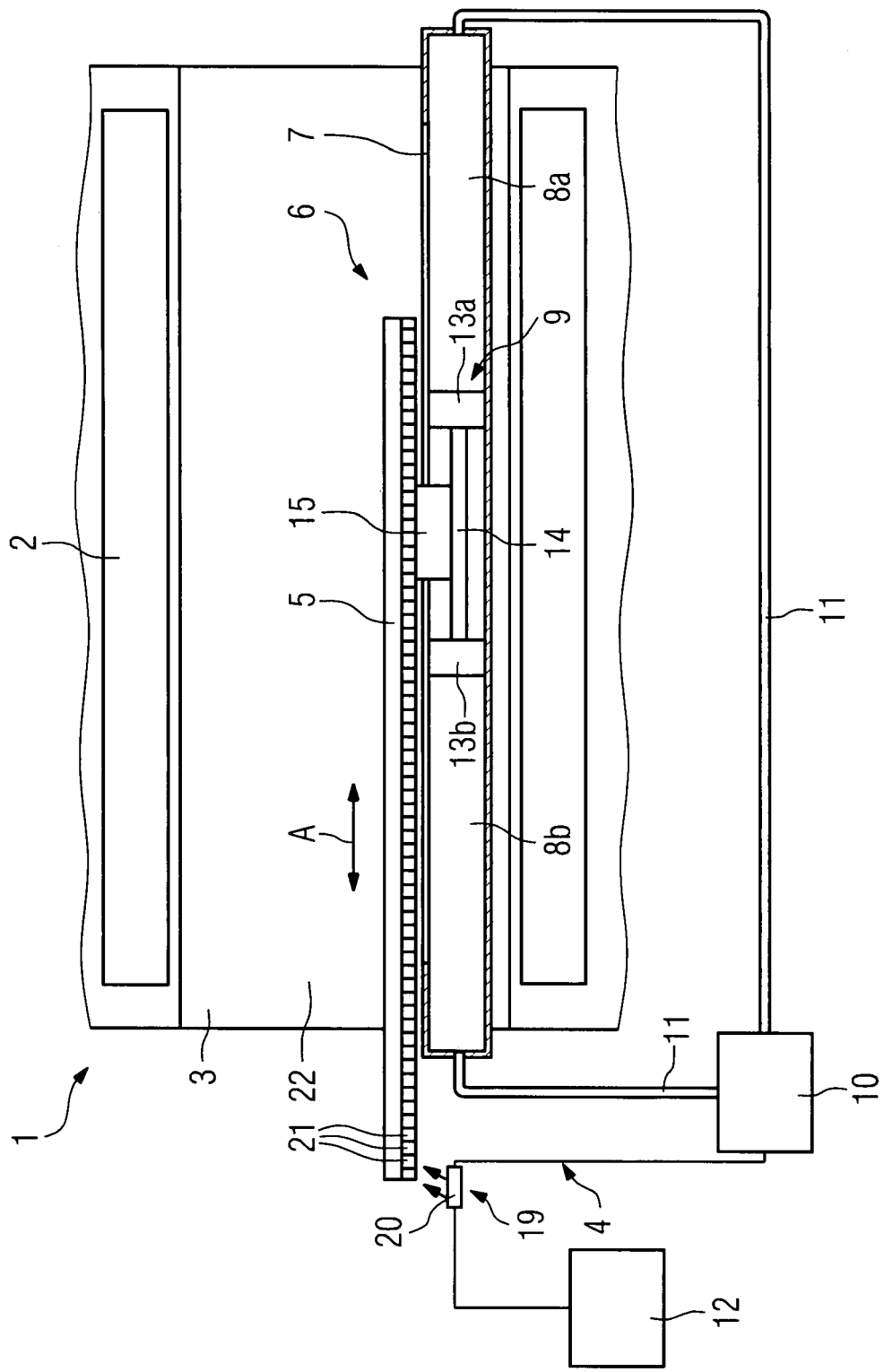
FIG. 1 a basic diagram of an inventive magnetic resonance system with an inventive patient support table and FIG. 2 a part view of the drive device of the patient support table depicted in FIG. 1.

FIG. 1 shows an inventive magnetic resonance system 1, including a magnetic field generation device 2, only shown in principle, for creating a basic magnetic field with a field strength of 7 T or more. The magnetic resonance system 1 is a cylindrical design and features a cylindrical patient chamber 3 (also frequently known as a patient cavity). Within this is arranged an inventive patient support table 4, comprising a table plate 5, which, as indicated by the double-ended arrow A, can be moved in and out of the patient chamber. To this end a drive device 6 is provided, comprising a pneumatic cylinder 7, which has two working areas 8a, 8b which are divided and sealed from each other using a piston 9. The working areas 8a, 8b can be supplied separately with a working medium, for example simple compressed air, or working medium can be sucked out of them to create a local vacuum. A pump 10 is used to do this, said pump being connected to the working areas via corresponding hose connections 11. Assigned to the pump is a control device 12 which controls the operation of the pump.

The piston 9 features two piston sections 13a, 13b which delimit or seal off the respective working area 8a, 8b. The two piston section 13a, 13b are connected to each other via a connecting rod 14. A connecting element 15 is arranged in its turn on the connecting rod 14, with this connecting element for its part being permanently connected to the table plate 5. This means that the movement of the table plate 5 is directly coupled to that of the piston 9, meaning that the plate moves directly along with the piston 9 as it moves axially within the pneumatic cylinder 7. The table can thus be moved pneumatically.

Figure 2:
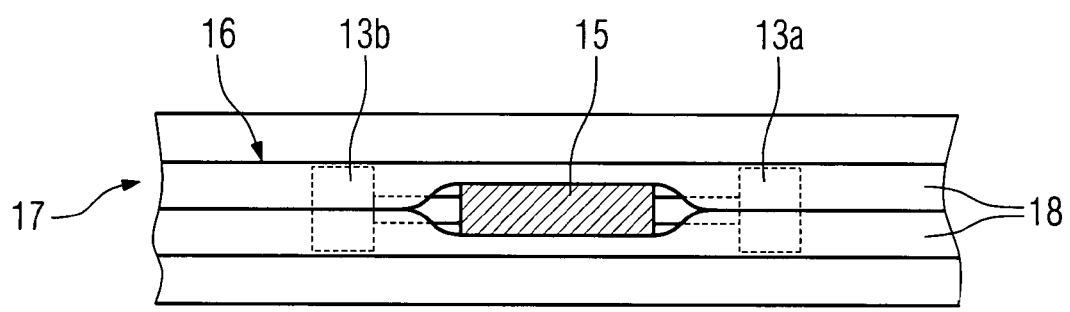

As can be seen from FIG. 1, the connecting element 12, which is embodied in the shape of a plate for example, is brought out for connection to the table plate 5 from the inside of the pneumatic cylinder. Since the table plate 5 can be moved out of the patient chamber 5 completely and back into this chamber again, the piston 9 and with it the connecting element 15 consequently essentially moves over the entire length of the cylinder. To make possible this movement of the connecting element which passes through the cylinder but simultaneously to guarantee that the working areas are sealed, see FIG. 2, the pneumatic cylinder 7 is provided on its upper side with a longitudinal cutout 16 extending over the major part of its length, in which a seal element 17 is arranged, comprising two separate sealing lips 18, of which one is attached to the left-hand side of the longitudinal cutout 16 and the other is attached to the right-hand side of the longitudinal cutout. Both sealing lips lie directly against each other when performing their original sealing function, as is shown in FIG. 2. They lie against each other such that sufficient sealing of the relevant working area 8a, 8b is provided. The system is so firm that a neither a considerable increase in pressure nor a considerable decrease in pressure, which occurs within the framework of the movement or of the pump operation, moves the sealing lips 18 apart and opens them. Instead of the lips sealing directly against each other, it is obviously also conceivable for the sealing lips 18 to overlap sufficiently.

However, as FIG. 2 further shows, the sealing lips 18 in the areas in which they are penetrated by the connection element 15 are pushed apart from each other, meaning that the sealing element 17 is opened locally. Immediately before and after this opening of the sealing element 17 the sealing lips 18 close again. The sealing lips 18 are suitably elastic, so that they open easily but equally relax immediately again and return to the position in which they form a tight seal with each other. To this end they consist of a suitable flexible and elastic plastic material and are correspondingly dimensioned in their length or thickness. In the area of the two sections 13a, 13b of the piston shown only by dashed lines in FIG. 2 the two sealing lips 18 seal again tightly against each other, so that the two working areas 8a, 8b adjoining the piston sections 13a, 13b can be completely sealed.

If it is now assumed that compressed air is pushed into the piston space 13a and compressed air is sucked out of the piston space 13b, then, based on FIG. 1, the piston 9 and thereby the table plate 5 will be moved to the left. In relation to FIG. 2 this would mean that the connecting element 15 also moves to the left. With the movement the sealing element 17 would be successively opened to the left, whereas to the right, as the connecting element 15 passes, the two sealing lips 18 close again.

As already described the control device 15 is provided for control of the pump and thereby of the movement operation of the drive device 6. To make exact positioning possible, a position detection device 19 is also provided, comprising a sensor 20 which defects suitable position markings 21 on the table plate 5. In the example shown this sensor 20 is an optical sensor which forms a light barrier with the typically reflective markings 21. The sensor 20 is in a fixed position, which means that, as a result of the position markings 21 arranged in a defined grid, it is thus easily possible to detect the exact movement and position of the table plate 5.

Obviously the position detection device 19 communicates with the control device 12. This now controls the pump operation depending on the position detection results, so that an exact position can be moved to or also, if the table plate is approaching the predetermined position, the speed can be varied accordingly.

The table plate 5 itself is supported in a manner not shown in any greater detail on the inner wall 22 of the patient chamber 3 to allow movement, for example via suitable guide rails, which can also be embodied as telescopic rails and also support the table plate in the area outside the patient chamber, or in the form of roller guides etc. The movement or sliding support is such that the weight of the table plate 5 is not supported or is only supported to a negligible extent on the connection element 15 and thereby on the piston 9.

An arresting device not shown in any greater detail here can be provided in the area of this movement or sliding guide, but also at another location, in order to lock the table plate 5 into the end position adopted. This means that the locking is not performed via the pneumatic cylinder 7 or the drive device 6, but via a separate arresting means, for example in the form of a mechanical detent, which for example fixes the table plate in the form of a detent pin or a detent clamp etc. The detent can also be provided as a type of arresting stop, meaning that the table plate 5 is for example moved on exit and also on entry against corresponding end stops which then lock the plate directly into place.

The invention claimed is:

1. A patient support table for a magnetic resonance system, comprising:
    a table plate that moves into and out of a patient chamber of the magnetic resonance system;
    a drive device comprising a pneumatic cylinder that moves the table plate, wherein the pneumatic cylinder comprises a radial opening running along the pneumatic cylinder;
    a piston arranged on the pneumatic cylinder and coupled to the table plate that divides the pneumatic cylinder to two working areas;
    an arresting device that locks the table plate;
    a connecting element passing through the opening for connecting the piston with the table plate; and
    a sealing element that is slit and penetrated by the connecting element through the slit to seal the opening,
    wherein the piston comprises two piston sections connected via a connecting rod and the table plate is connected to the connecting rod,
    wherein the sealing element comprises two sealing lips abutting each other or overlapping and extending over a portion of a length of the pneumatic cylinder, and
    wherein the two sealing lips consist of sufficiently flexible and elastic material which is moved apart over the connection element and moves back together or overlaps again once the connection element has passed.

2. The patient support table as claimed in claim 1, further comprising a position detection device that determines a position of the table plate and an operation of a pump coupled to the working areas of the pneumatic cylinder is controlled based on a result of the detection.

3. The patient support table as claimed in claim 2, wherein the position detection device is an optical device.

4. The patient support table as claimed in claim 1, wherein the two working areas are supplied separately with a working medium.

5. The patient support table as claimed in claim 1, wherein the magnetic resonance system comprises a magnetic field generation device that creates a magnetic field of 7 T or more.

6. A magnetic resonance system, comprising:
    a magnetic field generation device that creates a magnetic field of 7 T or more; and
    a patient support table comprising:
        a table plate that moves into and out of a patient chamber of the magnetic resonance system,
        a drive device comprising a pneumatic cylinder that moves the table plate, wherein the pneumatic cylinder comprises a radial opening running along the pneumatic cylinder,
        a piston arranged on the pneumatic cylinder and coupled to the table plate that divides the pneumatic cylinder to two working areas,
        an arresting device that locks the table plate,
        a connecting element passing through the opening for connecting the piston with the table plate, and
        a sealing element that is slit and penetrated by the connecting element through the slit to seal the opening,
    wherein the piston comprises two piston sections connected via a connecting rod and the table plate is connected to the connecting rod,
    wherein the sealing element comprises two sealing lips abutting each other or overlapping and extending over a portion of a length of the pneumatic cylinder, and
    wherein the two sealing lips consist of sufficiently flexible and elastic material which is moved apart over the connection element and moves back together or overlaps again once the connection element has passed.

7. The magnetic resonance system as claimed in claim 6, wherein the two working areas are supplied separately with a working medium.

* * * * *